United States Patent
Haider et al.

(10) Patent No.: US 9,717,621 B2
(45) Date of Patent: Aug. 1, 2017

(54) UNIVERSALLY ADJUSTABLE CERVICAL COLLAR

(71) Applicant: UNIVERSITY BRACES, LLC, San Diego, CA (US)

(72) Inventors: Thomas T. Haider, Sante Fe Springs, CA (US); Chih-Chuan Wang, Longin Taichung (TW)

(73) Assignee: University Braces, LLC, San Diego, CA (US)

( * ) Notice: Subject to any disclaimer, the term of this patent is extended or adjusted under 35 U.S.C. 154(b) by 0 days.

(21) Appl. No.: 14/857,665

(22) Filed: Sep. 17, 2015

(65) Prior Publication Data
US 2016/0000597 A1 Jan. 7, 2016

Related U.S. Application Data

(63) Continuation of application No. 12/927,811, filed on Nov. 24, 2010, now abandoned.

(51) Int. Cl.
*A61F 5/00* (2006.01)
*A61F 5/055* (2006.01)

(52) U.S. Cl.
CPC .................... *A61F 5/055* (2013.01)

(58) Field of Classification Search
CPC ....................................... A61F 5/055
USPC ............................. 128/97.1, 845; 602/18, 32
See application file for complete search history.

(56) References Cited

U.S. PATENT DOCUMENTS

| | | |
|---|---|---|
| 5,005,563 A | 4/1991 | Veale |
| RE34,714 E | 8/1994 | Burns et al. |
| 5,688,229 A * | 11/1997 | Bauer ............... A61F 5/055 128/DIG. 23 |
| 6,036,664 A | 3/2000 | Martin, Sr. et al. |
| RE36,745 E | 6/2000 | Rudy, Jr. et al. |
| 6,254,560 B1 | 7/2001 | Tweardy et al. |
| 6,726,643 B1 | 4/2004 | Martin |
| 7,674,234 B2 | 3/2010 | Calco et al. |
| 2004/0204666 A1 | 10/2004 | Marsh |
| 2005/0113728 A1 | 5/2005 | Heinz et al. |
| 2007/0027418 A1 * | 2/2007 | Calco ............... A61F 5/055 602/18 |
| 2012/0130295 A1 | 5/2012 | Haider |

* cited by examiner

*Primary Examiner* — Ophelia A Hawthorne
*Assistant Examiner* — Caitlin Carreiro
(74) *Attorney, Agent, or Firm* — Wilson Sonsini Goodrich & Rosati

(57) ABSTRACT

An adjustable cervical collar is in the form of a u-shaped base with a front joined to a pair of rearwardly extending wings. Left and right chin supports are pivotally connected at their distal ends to the distal ends to of respective wings with a chin piece connected between the upper proximal ends of the chin supports. An adjustable latch is individually coupled between each wing and the lower proximal end of the associated chin supports. Preferably the latch is in the form of 1) an arcuate slot in each wing arranged around the respective pivot axis with a track formed on opposite sides of the slot and 2) a retractable locking pin carried by each chin support and movable within the respective slot, the locking pins adapted to engage the ribs in the respective track to releasably lock the chin support to the respective wing.

5 Claims, 12 Drawing Sheets

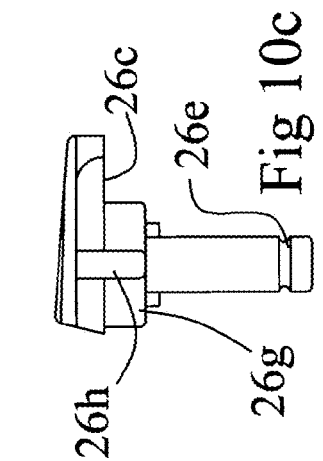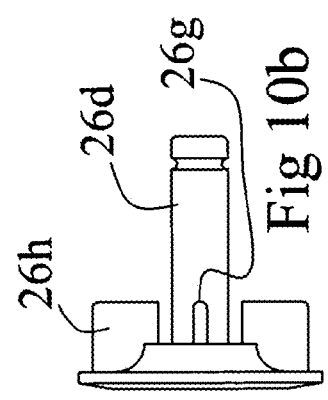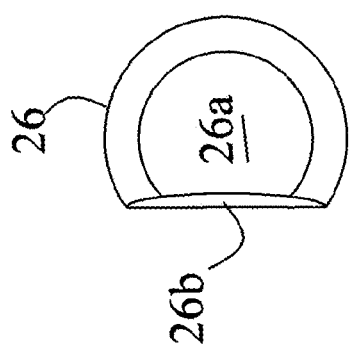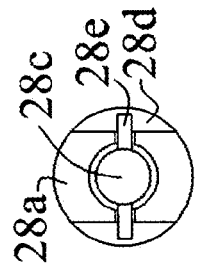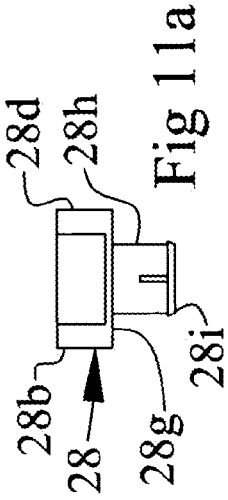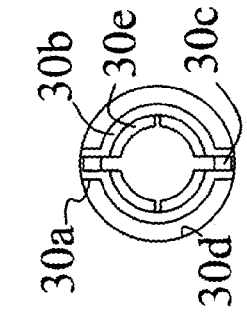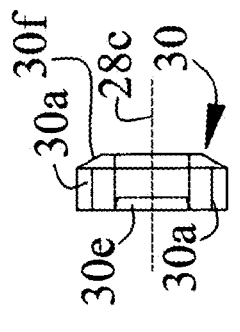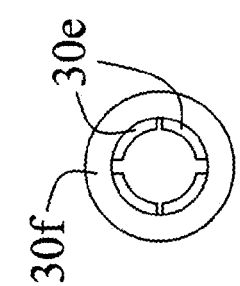

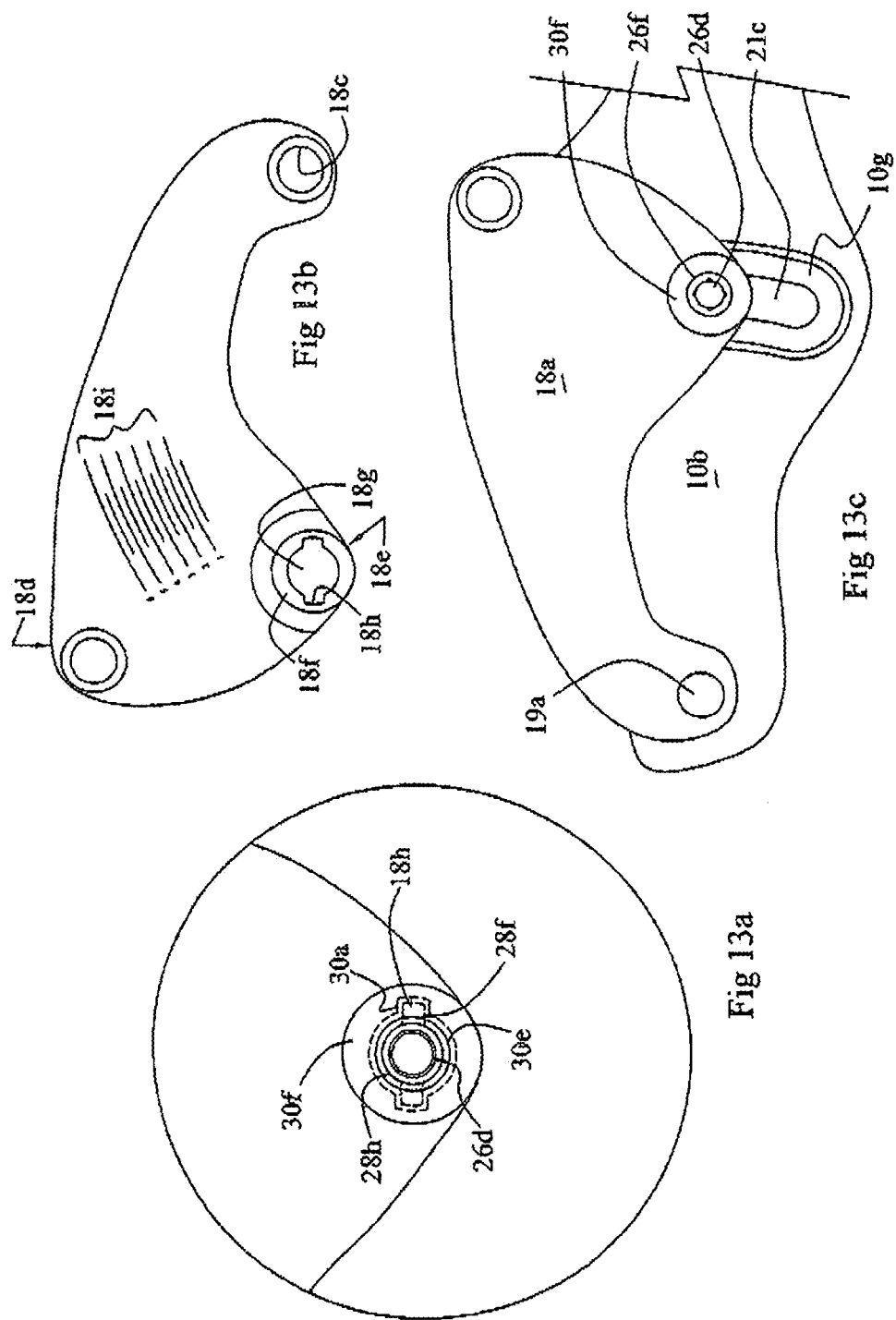

UNIVERSALLY ADJUSTABLE CERVICAL COLLAR

FIELD OF THE INVENTION

The present invention relates to portable neck braces and more particularly to a cervical collar that is universally adjustable to provide the quality of "one size fits all", easy to install and provides a comfortable fit to enable a patient to wear the collar in compliance with the physician's orders.

BACKGROUND OF THE INVENTION

Portable neck braces have been used for years to immobilize the head and neck of a patient and put them in proper alignment after an injury as a result of trauma or disease. Cervical collars are generally of two types, either off-the-shelf-stock type which comes in a variety of sizes to accommodate a population of patients or collars which have certain adjustable features to reduce or hopefully eliminate the need for a variety of sizes.

The art relating to portable neck braces and cervical collars is crowded, particularly in the patent literature. The various prior art braces have certain shortcomings, leaving a need to be filled. For example, the portion of the brace which supports the chin needs to be adjustable in a vertical direction to accommodate different anatomies. In addition the chin support needs to be adjustable to allow the head to be canted to one side or the other; i.e. tilted relative to the vertical. In addition to those needs the brace or collar must be economical to manufacture, sturdy, easy to install, comfortable to wear and easy to adjust.

With respect to the prior art noted in certain patents see U.S. Pat. No. 7,674,234, ("234 patent") which discloses a cervical collar that uses a somewhat complicated rack and pinion arrangement to raise and lower a chin strap; however, there is no ability to adjust the chin strap supports independently so the patient's head can be canted to one side (tilted relative the vertical) to accommodate a required anatomical constraint. U.S. Pat. No. 6,254,560 discloses another somewhat complicated cervical collar in which only vertical adjustment appears to be possible. U.S. Pat. No. 5,005,563 discloses a cervical collar in which vertical adjustment is accomplished by means of a threaded groove and a worm screw. US Pub. No. 2004/0204666 A1, discloses a complicated cervical spine brace and traction device in which a rear portion abutting the patient's occipital region of the skull can be adjusted vertically by means of two lead screws and gear boxes. It would not appear to be user friendly or economical to manufacture. Also see U.S. Pat. Nos. 6,726,643, 6,036,664, Re Nos. 34,714, and 36,745 and US Patent Appln. 2005/0113728 A1.

The universally adjustable cervical collar of the present invention addresses the short comings of the prior art and has achieved significant commercial acceptance in a short period since it was introduced into the market earlier this year. As an example, the present invention is fairing quite well against a competitive cervical collar generally following the teachings of the '234 patent.

SUMMARY OF THE INVENTION

A cervical collar in accordance with this invention comprises a u-shaped base with a front, adapted to extend over the sternum of a patient, joined to a pair of rearwardly extending left and right wings or arms, adapted to extend over respective shoulders of the patient. Left and right generally planar chin or jaw supports are pivotally connected to the approximate distal ends of the associated wings and extend forwardly to a proximal end defining upper and lower proximal sections.

A chin piece, generally in the form of a semi-rigid strap, is pivotally mounted at each end to the upper proximal sections of the chin supports. An adjustable latching system in the form of a retractable latch mechanism is individually coupled between each of the arms and the lower proximal section of the associated chin supports. Each latch is arranged along an arc or sector of a circle centered on the associated axis about which the respective chin support is pivotally mounted on its associated wing.

In the preferred embodiment the latch mechanism includes a curved track positioned on each of the arms or the chin supports with a releasable locking pin positioned on the other member. Most preferably an arcuate slot is formed in the wings with a track having ribs or teeth extending inwardly from each side of the slot. A retractable locking pin is carried by the chin supports and provided with outwardly projecting ribs or teeth for engaging adjacent teeth on the track when in the locked position. When the pin is retracted from its locked position the proximal end of the chin supports are free to move relative to the wings and independently of each other. This allows the chin piece to not only be raised or lowered but canted at an angle to the base, i.e. to the vertical as is illustrated in FIG. 7.

BRIEF DESCRIPTION OF THE DRAWINGS

FIGS. 10a, and 10b, are a top plan view and a side view of the locking pin portion of the latch mechanism showing the anti-rotation stubs that fit into the receptacle (shown in FIGS. 11 and 12);

FIG. 10c is another side view of the locking pin, FIG. 10d is a top plan view of a metal retaining washer for securing the bottom of the locking pin in place in the receptacle to be described;

FIGS. 11a, 11b and 11c are a side view, a top plan view and another side view of the upper component of the receptacle, respectively; FIG. 11b shows the slots for receiving the anti-rotation stubs of the locking pin;

FIGS. 12a, 12b and 12c are a bottom plan view, a side view and a top plan view of rhe lower component, respectively;

FIG. 13a is an isolated view of the assembled locking pin (without the retaining washer) and receptacle in place in a the associate opening in a wing, looking toward the wing, showing in phantom lines the keyway stubs in the lower component with the anti-rotation ribs of the upper component seated in the slots formed in the stubs;

FIG. 13b is an exterior side view a chin support, showing the keyway slots for receiving the cooperating keyway stubs of the lower component of the receptacle;

FIG. 13c is an inside view (broken away) of the lower proximal section of one of the chin supports assembled to one of the wings showing the assembled locking pin and receptacle in place and the raised raceway on the inside of the wing.

DESCRIPTION OF THE PREFERRED EMBODIMENT

General Discussion of the Cervical Collar and Back Piece

Figure 1:
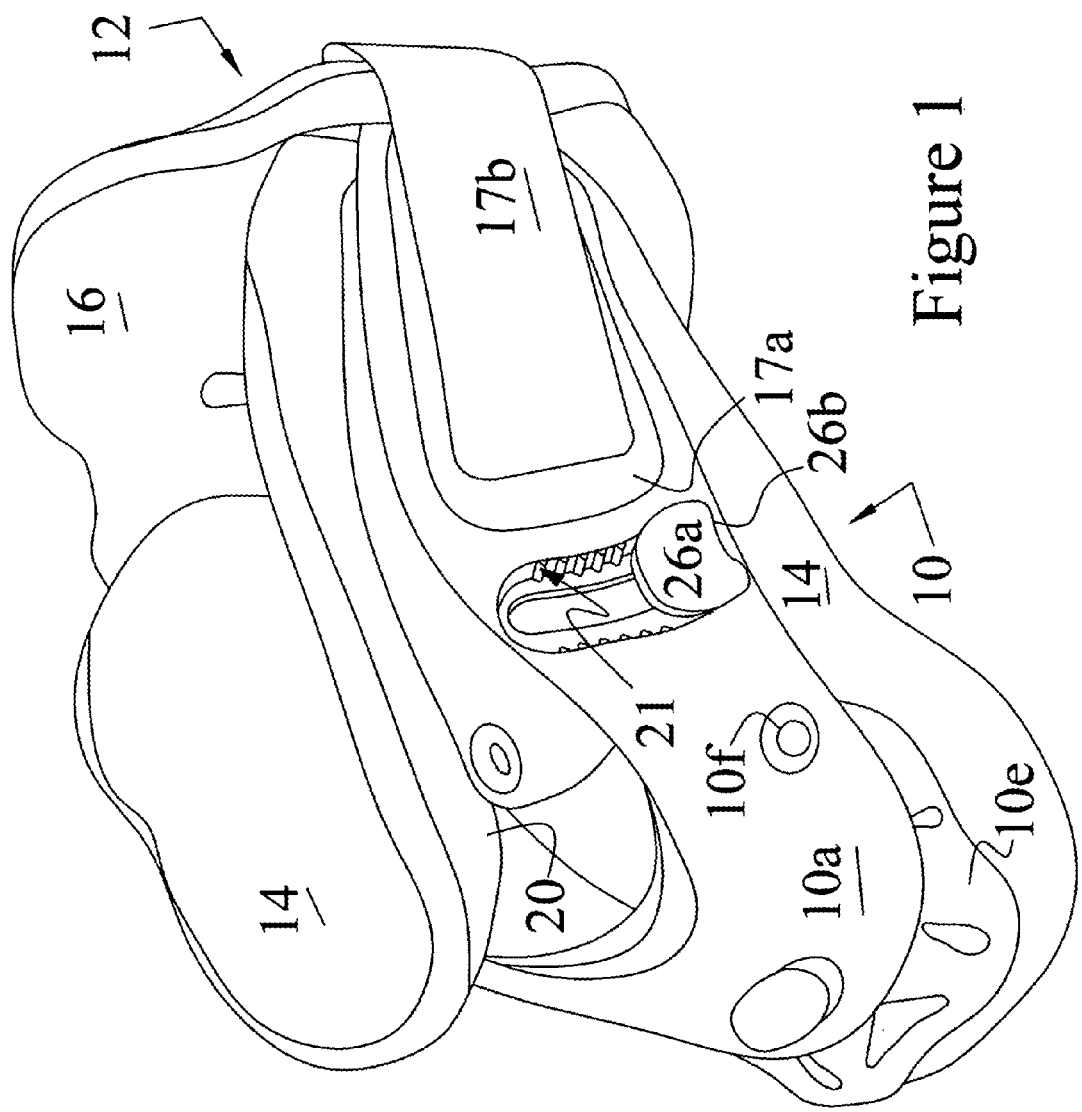
FIG. 1 is a side perspective view of the cervical collar together with the back piece forming a completed neck brace with foam lining in place for the comfort of a patient.
Figure 8:
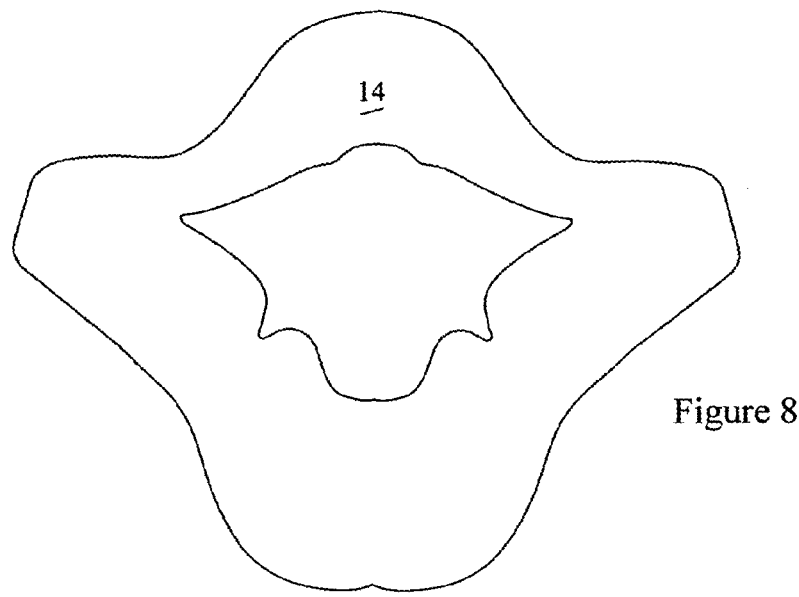
FIG. 8 is a plan view of the foam padding for the cervical collar.
Figure 9A:
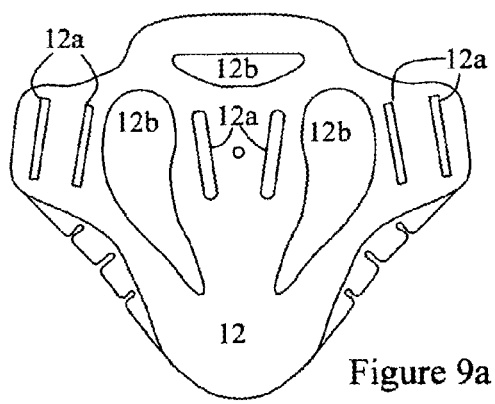
FIGS. 9a and 9b are top plan views of the back piece without the foam and of the foam, respectively.
Figure 9B:
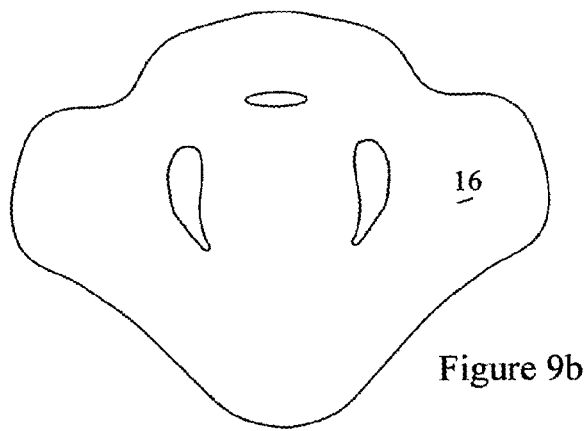
Figure 9C:
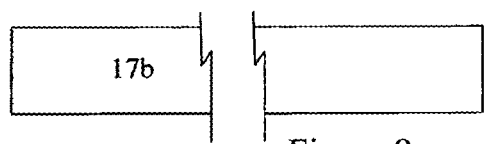
FIG. 9c is a plan view of the strap.

Referring now to the drawings and more particularly to FIG. 1, a cervical collar 10 and back piece 12 form a complete neck brace with foam lining segments 14 and 16 in place. The back piece is releasably secured to the collar via conventional hook and loop fasteners attached to the collar at 17a and to the underside of the strap 17b. The foam padding 14 for the collar, before installation, is shown in FIG. 8. The back piece 12 is shown in FIG. 9a with the slots 12a arranged to receive the strap 17b. The openings 12b serve to reduce the weight and increase the flexibility of the back piece. The foam padding 16 is illustrated in FIG. 9b. The foam padding may be seemed to the collar and the back piece, by means of hook and loop fasteners, not shown. The strap, 17b, is shown in FIG. 9c.

Referring now to FIGS. 2-7, the cervical collar 10 comprises a u-shaped base having a front section 10a, adapted to extend over a patient's sternum, joined to left (10b) and right (10c) rearwardly extending wings or arms, adapted to extend over a patient's shoulders. The wings terminate in distal sections 10d, (only the left one is shown). The base and back pieces are formed of a suitable polymeric material capable of retaining their shape while allowing some bending to allow the wings to conform to a patient's neck when secured thereto via the back piece. The collar base includes a more flexible extension 10e connected to the lower portion of the front section 10a by a pair of plastic rivets, 10f. The extension is arranged, with its underlying foam, to rest against the patient's upper chest.

Left and right generally planar chin supports 18a and 18b, respectfully, are pivotally connected at their distal ends 18c (see FIG. 13), via plastic rivets 19a, along generally horizontal axes 19b and 19c to the distal sections 10d of the wings of the base. The chin supports, which are located inwardly of the wings, define upper and lower proximal sections 18d and 18e, respectively, which collectively are sometimes referred to as the proximal end of the chin supports, as shown. The chin supports may be located toward the neck of a patient, i.e., inwardly of the wings, when the collar is being worn (See FIGS. 7 and 15c). A chin piece 20, generally shaped to accommodate a patient's chin, is pivotally connected at each end to the upper proximal sections 18d of the chin supports, via plastic fasteners 19d, as shown.

Discussion of the Adjustable Latching System

The adjustable latching system comprises an adjustable latch mechanism 22 (herein after "an adjustable latch" or "latch") individually coupled between each arm or wing (10b,10c) and the associated chin support (18a,18b). Each adjustable latch is arranged along an arc about the respective pivot axis (19b,19c) to allow the proximal end of each chin support to be moved independently along the associated wing. The arc may be considered as a sector of a circle with its center at the respective pivot axis as shown. More specifically, the preferred adjustable latch comprises a curved track 21 formed on upstanding wall 21b surrounding an elliptical slot 21c, following the arc in each wing (FIG. 3) and a retractable locking pin 26 slidably mounted in a receptacle 28/30 carried by the associated chin support, the locking pin being arranged to releasably engage the track, as will be explained in more detail.

Figure 2:
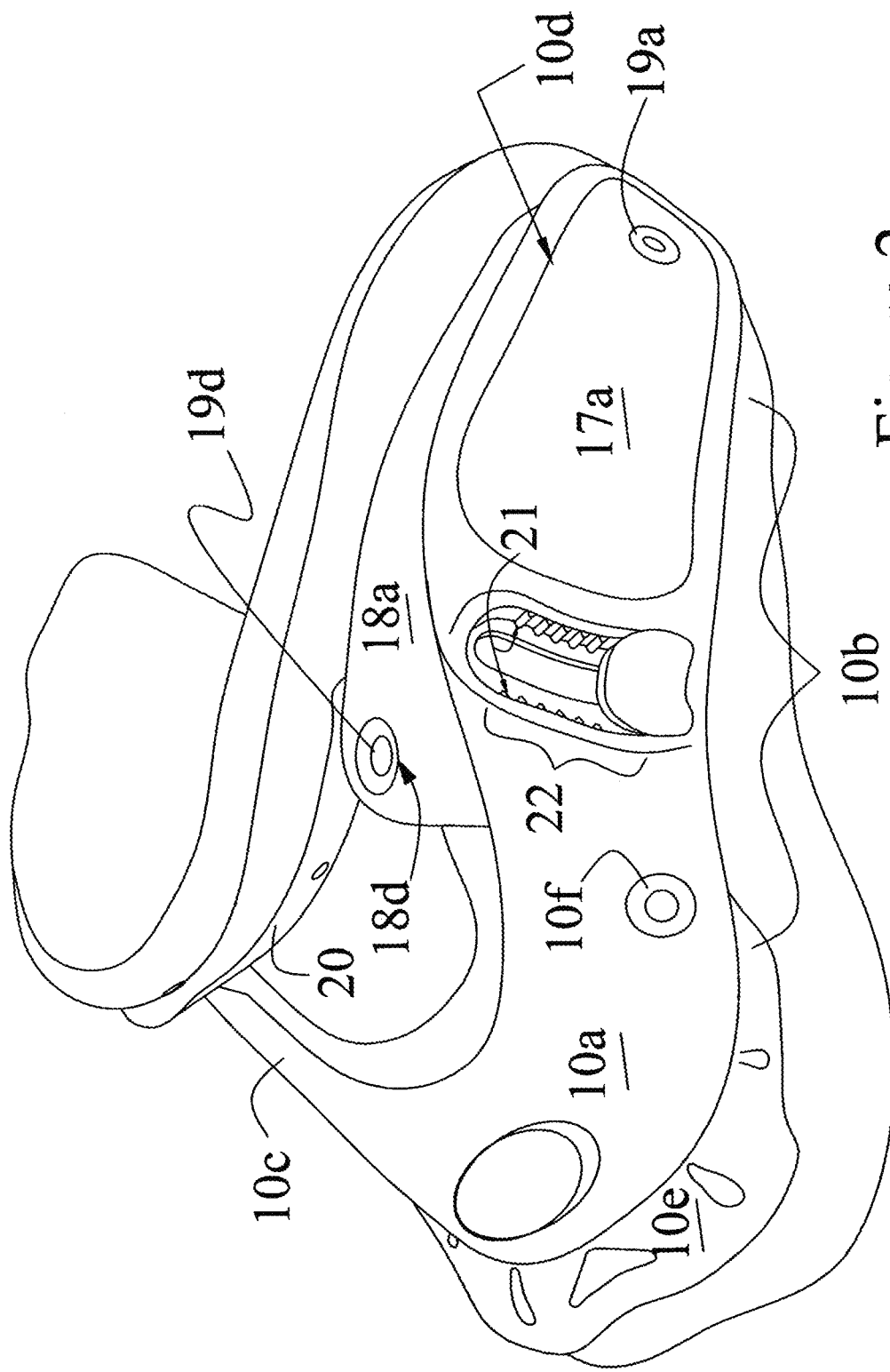
FIG. 2 is a slightly altered side view of the cervical collar alone with the foam lining in place and the locking pin portion of the retractable latch mechanism (visible on the left side of the collar) shown in the locked position.
Figure 3:
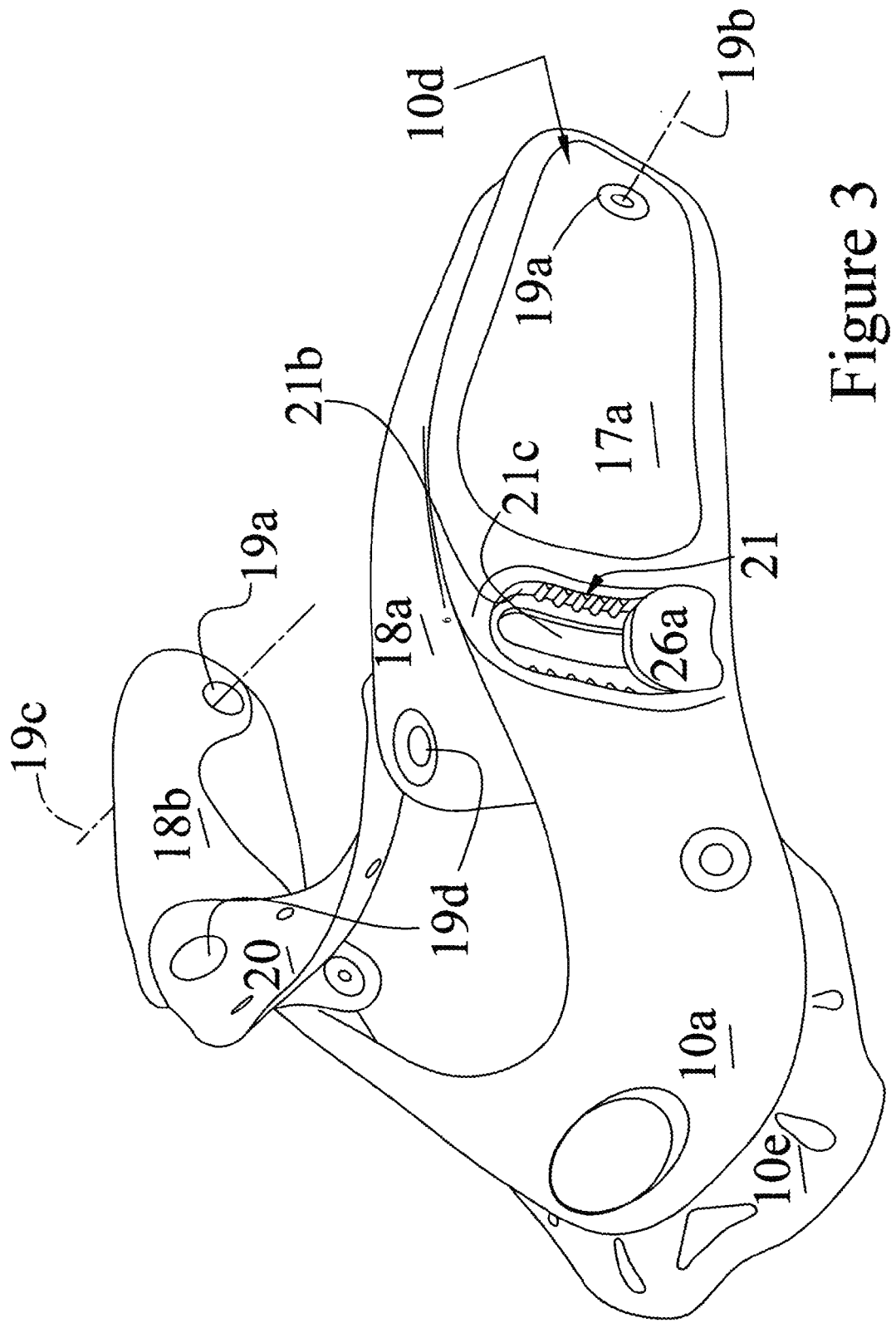
FIG. 3 is the same side view of the collar without the foam showing the chin piece in its lowest position.
Figure 4:
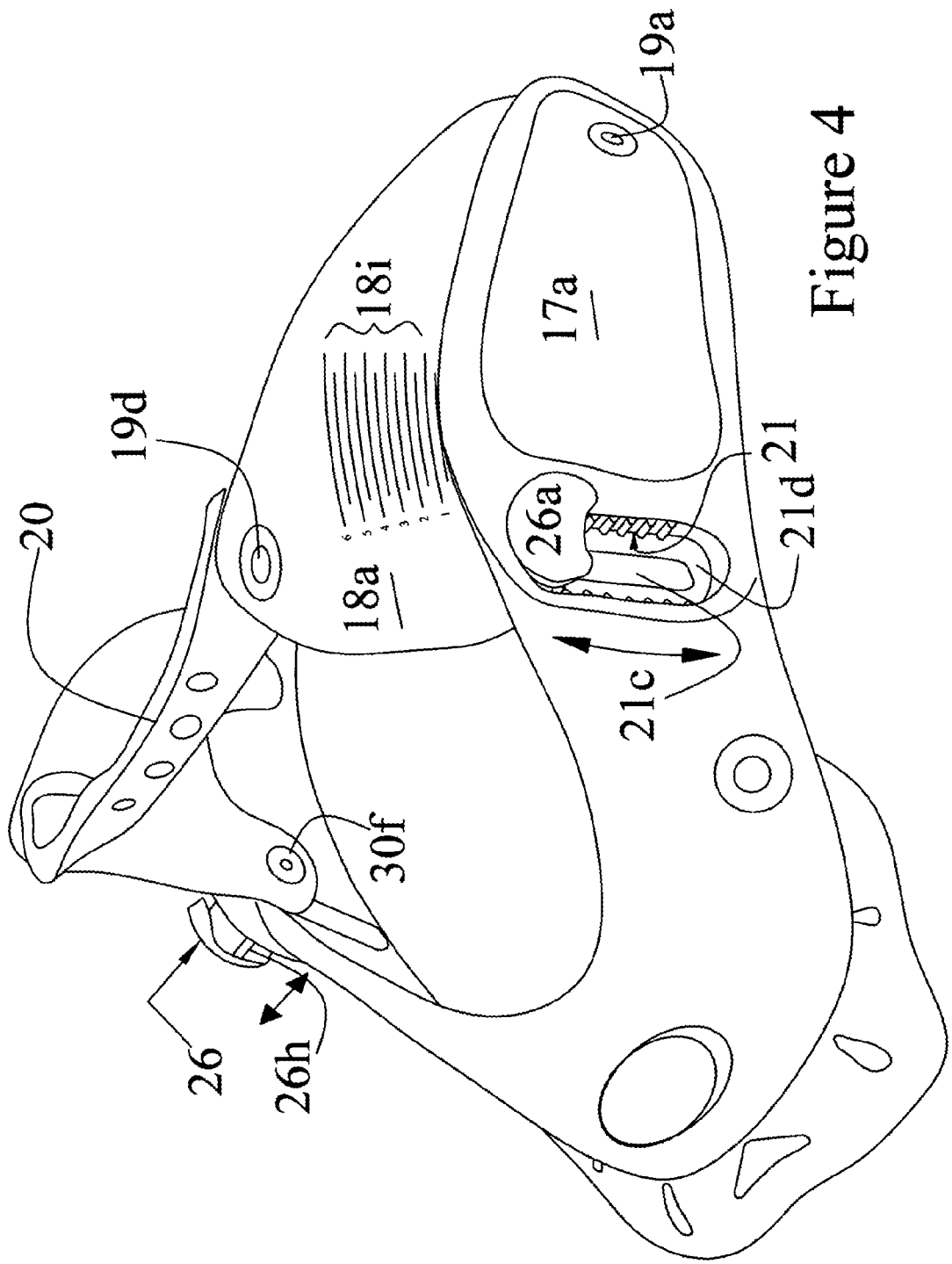
FIG. 4 is the side view of the collar with the chin piece in its highest position and the locking pins in their retracted or unlocked positions.
Figure 5:
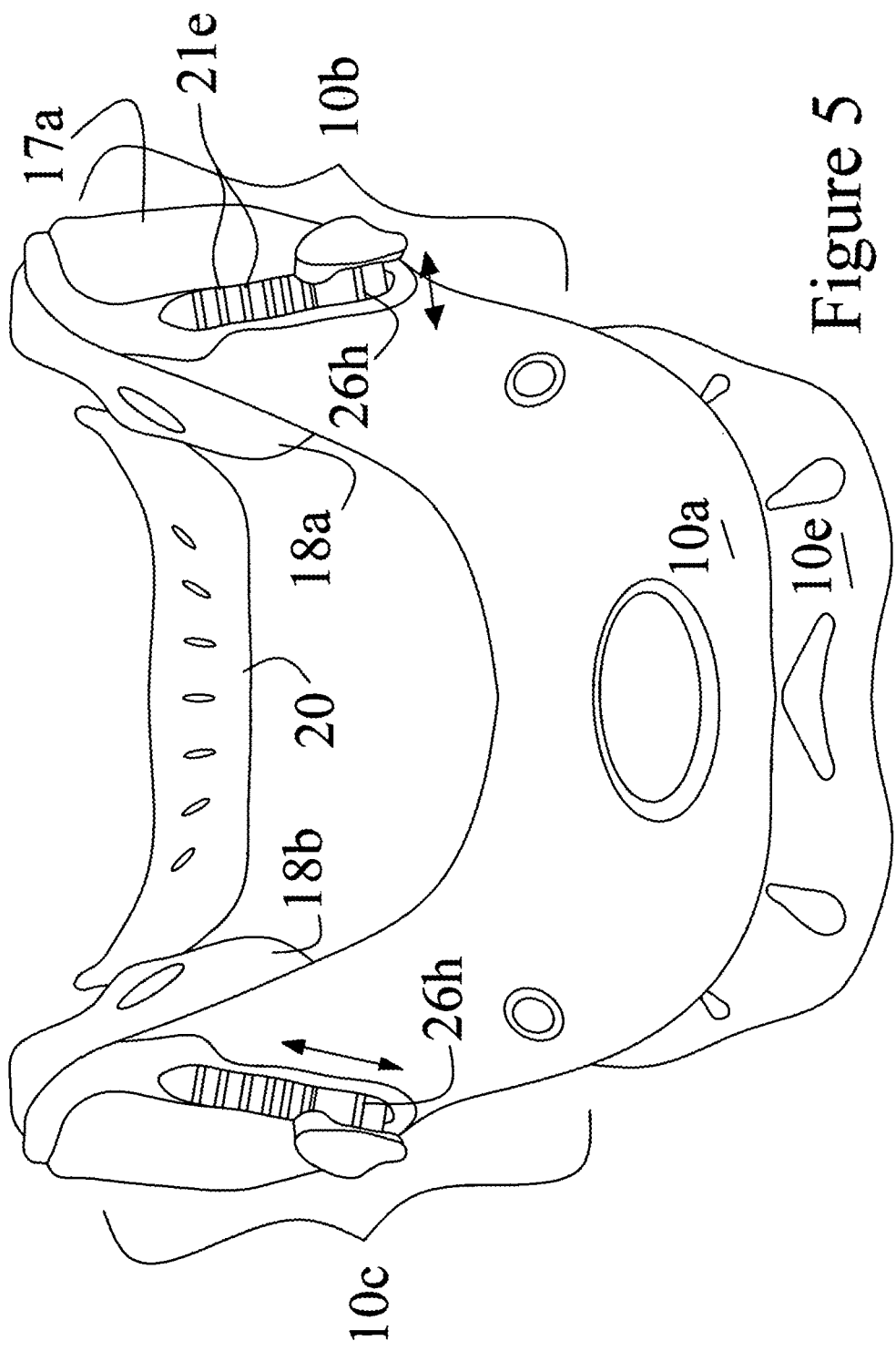
FIG. 5 is a front perspective view of the collar with the chin piece in its lowest position and the locking pins in their retracted positions.
Figure 6:
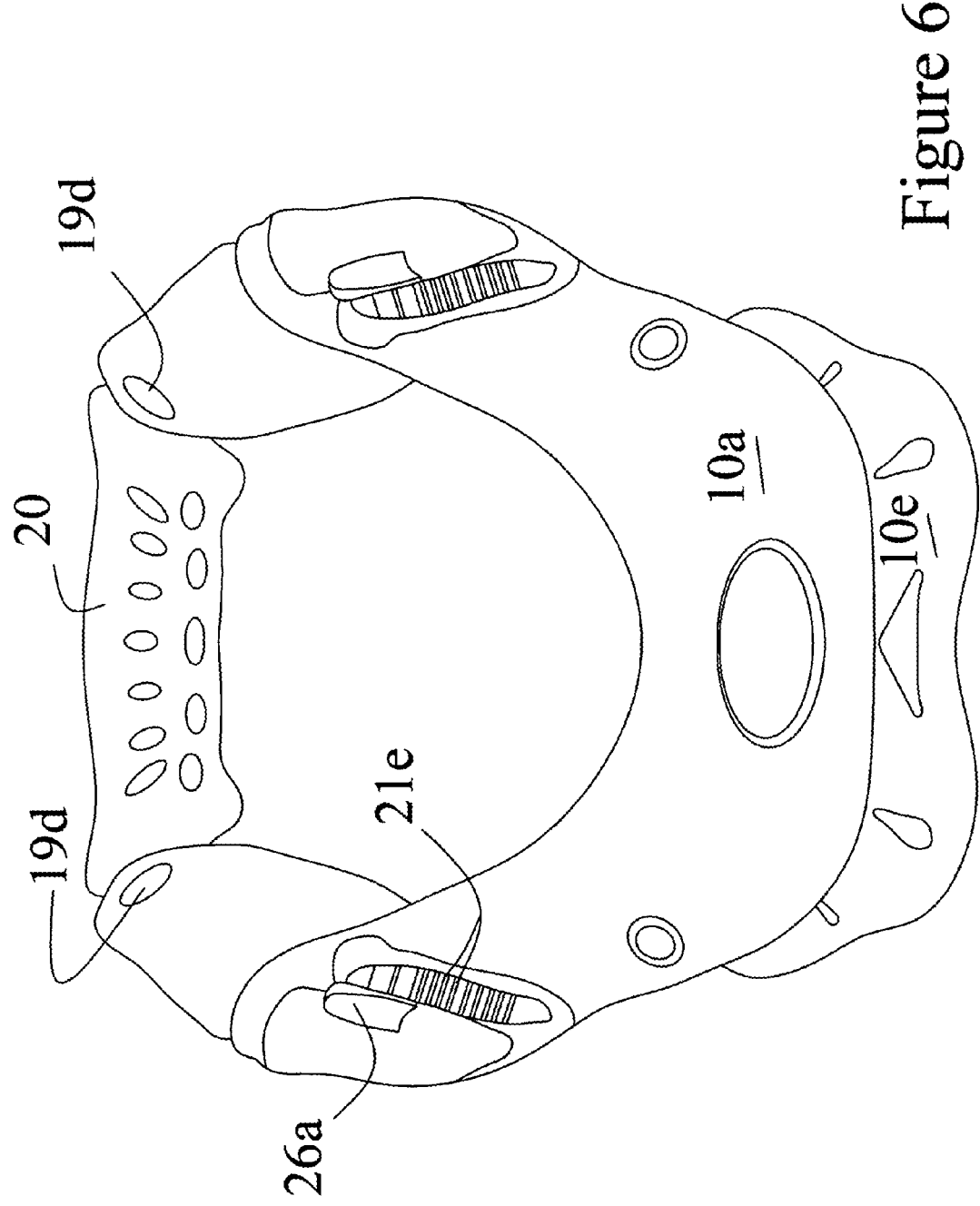
FIG. 6 is the same view as FIG. 5 with the chin piece in its highest position.
Figure 7:
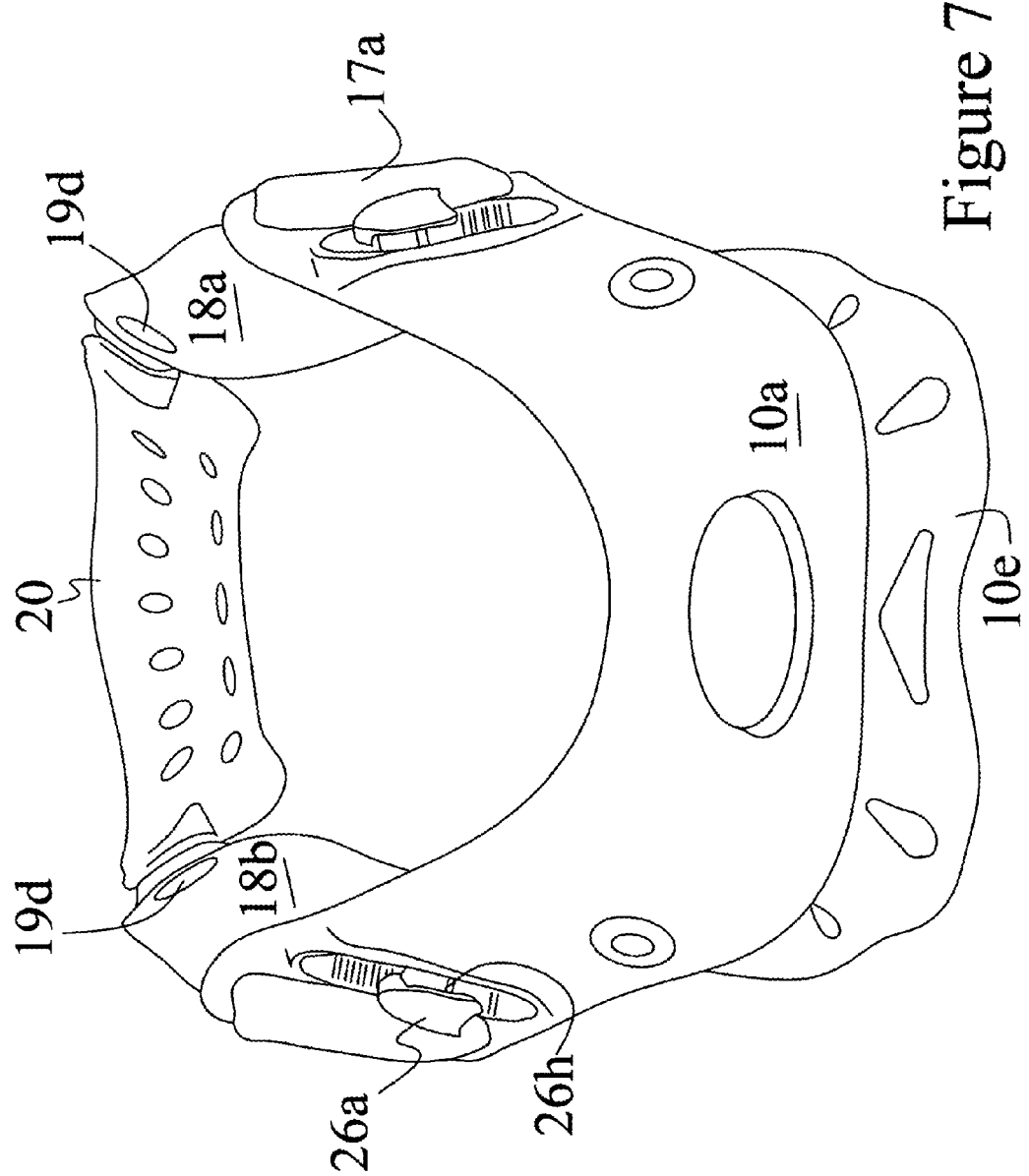
FIG. 7 is the same view as FIG. 5 with the chin piece in a canted position causing the patient's chin and head to assume an angle to vertical.

The range of the movement, or the chin supports, is illustrated in FIGS. 2-7, in which FIGS. 2, 3 and 5 show the chin supports and the chin piece in their lowest position, while FIGS. 4 and 6 show the chin supports in their upper most position. FIG. 7 shows the chin supports in intermediate positions with the right support disposed at a lower elevation than the left support leaving the chin piece canted or inclined at an angle to the vertical (vs. perpendicular thereto).

FIGS. 1, 2 and 3 show the locking pins 26 (to be described) of the adjustable latches in their locked or deployed position, while FIGS. 4-7 show the latches in their retracted position.

Referring now to FIG. 10, the locking pin, 26, includes a rounded head 26a cut off on one side at 26b with an undercut portion 26c on the other side to accommodate a person's fingers in retracting the pin. The pin includes a depending spindle or shaft 26d with a slot 26e formed at its distal end to accommodate a retaining washer 26f to maintain the pin in the receptacle while allowing limited axial movement to accommodate the locking and unlocking motion.

The pin further includes anti-rotation stubs 26g to prevent the pin from rotating within the upper component 28 of the receptacle. Downwardly extending locking ribs 26h are arranged to engage adjacent radially extending ribs on the track formed in the wing to lock the associated chin support to the wing when the pin is in its locked position, as will become apparent.

Referring now to FIGS. 11-12, an upper component 28 of the receptacle is in the form of a sleeve with an intermediate annular flange 28a bisecting a top cup portion 28b from a lower portion 28h. This sleeve surrounds a through hole 28c and defines diametrically opposed posts 28d extending upwardly from the flange and defining slots 28e for receiving the anti rotation stubs 26g on the pin. The lower portion 28h surrounds the through hole and includes radially extending anti-rotation ribs 28f for engaging opposing slots 30c formed in the lower receptacle component 30, as will be explained. The lower surface 28g of the flange is arranged to engage an annular elliptical shelf 21d of the associated collar wing surrounding the arcuate slot 21c. See FIG. 4.

The lower component 30 is in form of a cup defining a continuation of the through hole 28c with an annular flange 30b interrupted by opposing keyway ribs 30a for engaging keyway slots 18h in the lower proximal section of an associated chin support. See FIG. 13a. The ribs 30a define internal slots 30c for receiving the ribs 28f of the upper component. An upper ring 30d is also interrupted by the ribs 30a. Four flexible retention flaps 30e extend inwardly and downwardly from the bottom, maintaining the upper component in place once assembled. The outer annular surface is labeled 30f.

FIG. 13b shows the outer surface of one of the wings and more specifically a raised annular surface 18f surrounding an opening 18g through which the ring 30c and ribs 30a extend in the assembled condition. The surface 18f includes two keyway slots 18h for receiving the cooperating ribs 30a to prevent, with the receptacle, the locking pin from rotating as it is moved along the slot and track as the respective proximal end of the chin support is raised or lowered.

During assembly the lower component 30 (except for the flange) is inserted into the opening 18g after the distal end of the chin support has been mounted to its respective wing. The lower portion 28h of the upper component 28 is then inserted through the slot and into the lower component and secured thereto by forcing the lip 28l through the opening 28c in the lower component until the retaining flaps 30e engage the lip 28i. The pin is then inserted through hole 28c and the retaining washer is forced into the groove 26e to retain the pin in place while allowing the pin limited axial movement to accommodate the locking and unlocking motion. (See FIG. 4)

FIG. 13c is an inside view of an assembled chin support and wing showing a raised surface 10g on the wing, surrounding the slot 21c, in the form of a raceway against which the raised surface 18f of the chin support slides during relative movement between the two members.

Each of the wings has indicia, 18i, on the outside thereof labeled 1-6 showing the extent of movement of each chin support relative the base. See FIGS. 4 and 13.

Figure 14A:
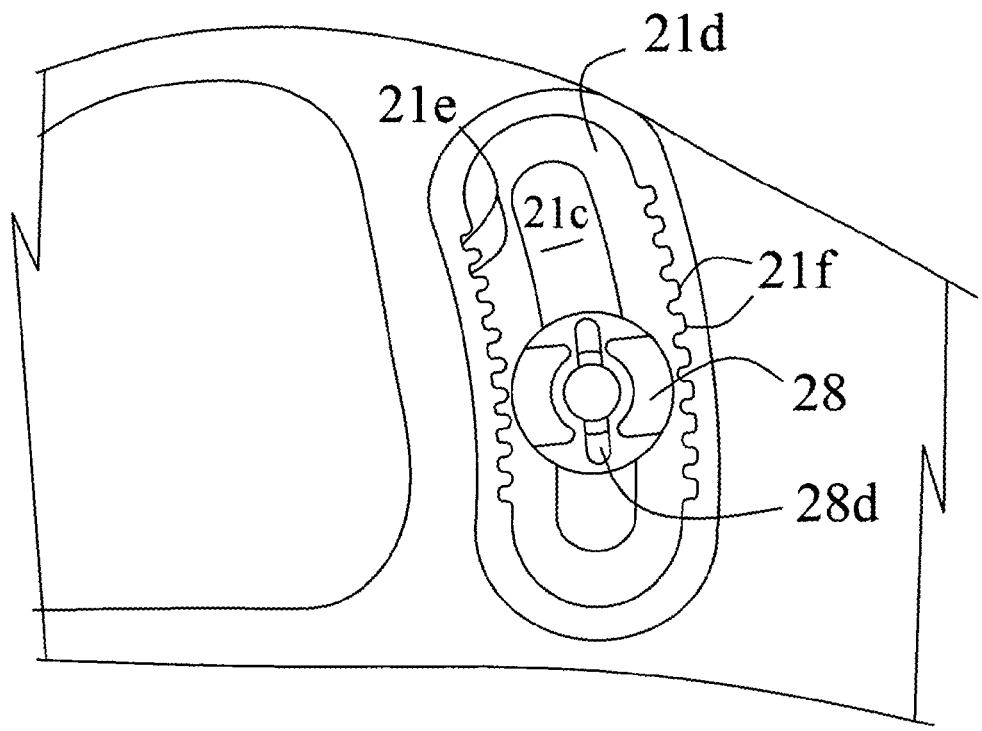
FIG. 14a is a broken away side view of the receptacle in place in the slot of one of the wings.
Figure 14B:
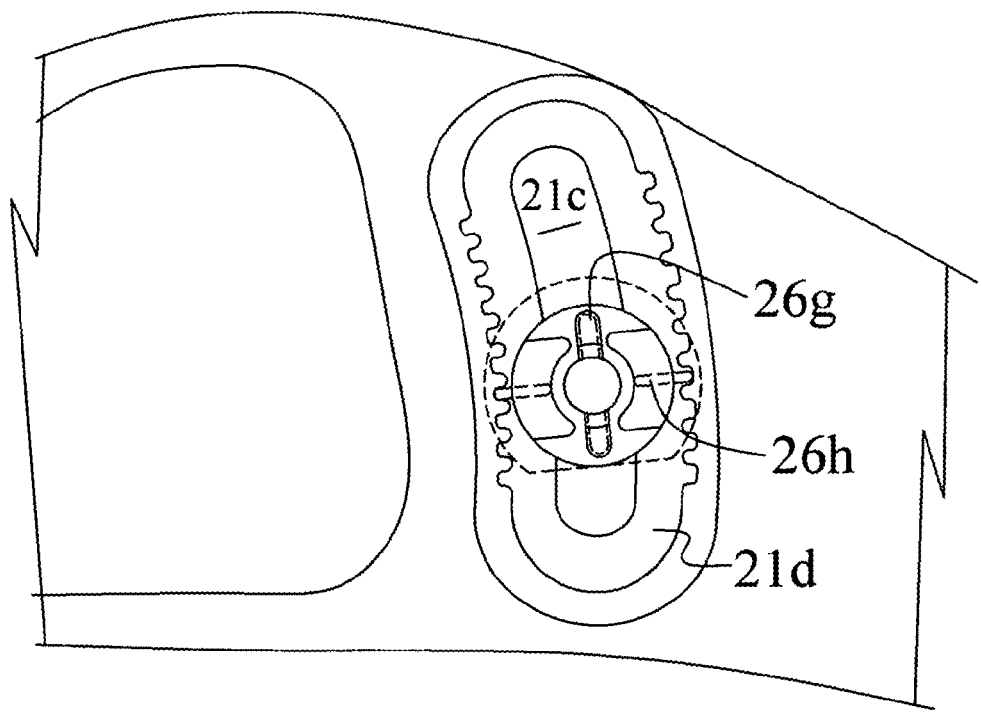
FIG. 14b is the same view of the receptacle and wing of FIG. 14a with a phantom view of the locking pin in a locked position showing the manner in which the ribs on the locking pin engage adjacent ribs on the track formed in the associated collar wing to freeze the rotational movement of the chin support relative to the associated collar wing.

The curved track portion of the adjustable latch will now be described in reference to FIGS. 14a and 14b. An arcuate slot 21c, following a sector of a circle, having its center at the respective pivot axis, is formed in each wing with an annular shelf 21d along which the lower surface 28g of the flange 28a of the upper component 28 of the receptacle rides when the chin support is raised or lowered. Extending above and surrounding the slot on opposed sides is the track, 21, with alternating ribs 21e and grooves 21f. FIG. 14a shows the receptacle in place with out the locking pin. FIG. 14b, shows, in phantom lines, the locking pin in place with the ribs 26h engaging two adjacent ribs in the track. This view also shows the anti-locking stubs 26g in place in the corresponding slots in the upper receptacle component.

Securing the Cervical Collar and Back Piece to a Patient

Figure 15C:
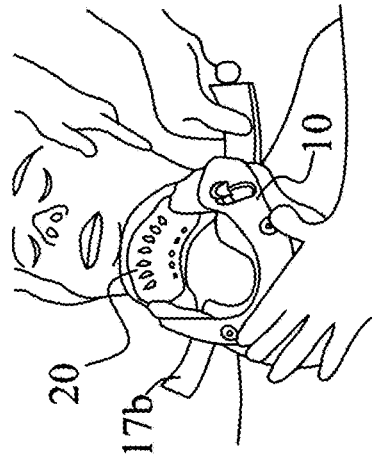
FIGS. 15a-15f are simplified perspective views of the collar illustrating one method of securing the invention in place.
Figure 15F:
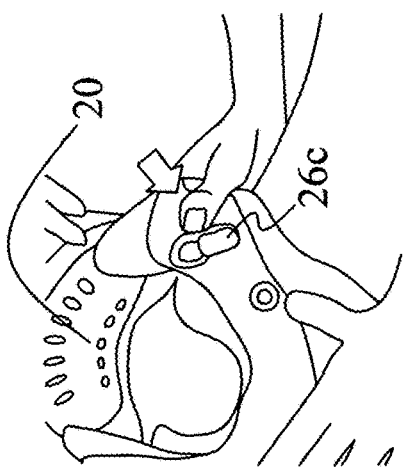
Figure 15B:
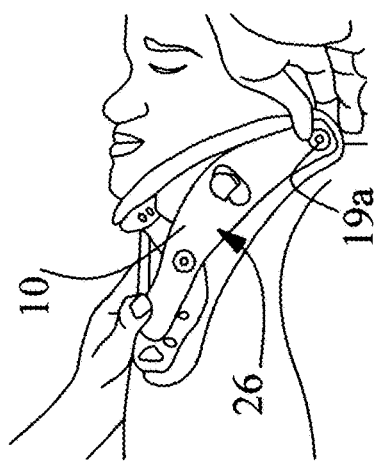
Figure 15E:
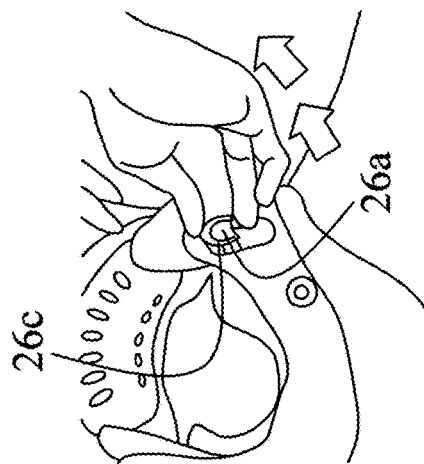
Figure 15A:
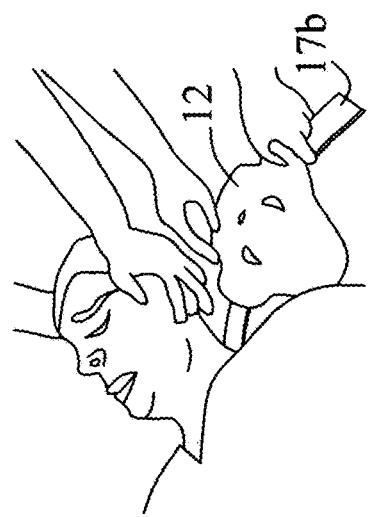
Figure 15D:
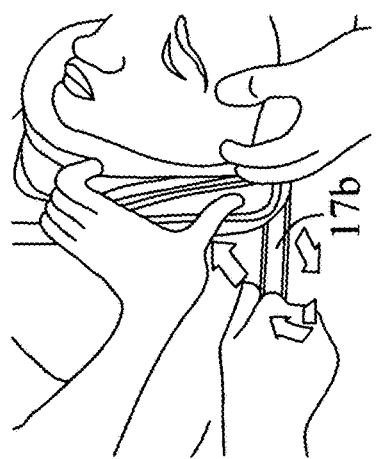

One method of using the present invention is illustrated in FIGS. 15a-15f. First, place the patient's head in neutral alignment as illustrated, then place the back piece behind the patient's head and carefully slide it towards the center to minimize the patient's pain as is shown in FIG. 15a.

Next place the collar under the patient's chin and chest, as is illustrated in FIG. 15b. The locking pins 26 may be used to adjust the collar to the appropriate level. For example, the heads 26c of the locking pins may be pulled outwardly and upwardly to adjust the collar's position.

Once positioned, place one hand on the collar and gently attach the strap 17b on the back piece 12 to the hooks 17a on the collar as is shown in FIGS. 15c and d.

For final adjustment pull the head 26a of the locking pin outward and upward to adjust the position of the collar. Last push the head 26a inward to lock the collar in place. See FIGS. 15e and f.

There has been described and illustrated a novel cervical collar and back piece which represents a significant improvement over the prior art. The collar is adjustable vertically to accommodate a wide range of patients; i.e., one size fits all. The collar also allows the chin piece to be inclined to accommodate a patient's anatomical constraints. Modifications and perhaps improvements of the invention will occur to those skilled in the art without departing from the spirit and scope thereof as defined in the appended claims.

What is claimed is:

1. A universally adjustable cervical collar comprising:
a) a u-shaped base having a front, adapted to extend over a patient's sternum, joined to left and right arms, adapted to extend over the patient's shoulders, the arms having proximal and distal ends and extending rearwardly from the proximal to the distal ends;
b) left and right chin supports pivotally connected along pivot axes to the distal end of respective arms of the u-shaped base and extending forwardly from the pivot axes to upper and lower front sections having tracks;
c) a left and a right adjustable latch mechanism coupled between each of the arms and the lower front sections of the respective chin supports, each latch mechanism being arranged along an arc arranged about the respective pivot axis to allow each chin support to be moved relative to the u-shaped base independently of the other chin support;
d) a chin piece disposed between the upper front sections of the chin supports; and
e) each latch mechanism being further arranged to lock the chin piece in a selected position, wherein the selected position of the left latch mechanism in an uppermost position is not affected by the selected position of the right latch mechanism in a lowermost position;
wherein the latch mechanism includes a curved track positioned on each of the arms or the chin supports and a releasable locking pin positioned on each of the chin supports or the arms, the tracks having a plurality of spaced inwardly projecting ribs and the locking pins having outwardly projecting ribs arranged to releasably engage adjacent ribs on the track; and
wherein the tracks comprise a pair of tracks located on each side of a curved slot.

2. The collar of claim 1 wherein each latch mechanism is arranged to raise or lower the chin piece.

3. The collar of claim 2 wherein the latch mechanism is arranged to allow the chin piece to be canted relative to the base.

4. The collar of claim 1 wherein the tracks are located on the arms with each chin support located inwardly of the respective arm toward a patient's neck when the collar is being worn by a patient.

5. The collar of claim 4 wherein the pin is arranged to travel within the respective slot and movable toward the respective arm to lock the chin support to the arm and away from the arm to allow the respective chin support to move relative to the arm, whereby the chin piece may be positioned at a desired height and angle relative to the u-shaped base.

* * * * *